United States Patent
Rhodes, Jr.

[11] 3,937,061
[45] Feb. 10, 1976

[54] DETECTOR FOR A CHROMTOGRAPH
[75] Inventor: Charles F. Rhodes, Jr., Richardson, Tex.
[73] Assignee: Sun Oil Company (Delaware), Dallas, Tex.
[22] Filed: Aug. 2, 1974
[21] Appl. No.: 494,248

[52] U.S. Cl. ................................. 73/27 R; 73/23.1
[51] Int. Cl.² ........................................... G01N 31/00
[58] Field of Search .......................... 73/23.1, 27 R

[56] References Cited
UNITED STATES PATENTS

| | | | |
|---|---|---|---|
| 3,228,230 | 1/1966 | Thiele | 73/27 R |
| 3,247,703 | 4/1966 | Burk | 73/23.1 |
| 3,590,628 | 7/1971 | Orr | 73/23.1 |
| 3,786,675 | 1/1974 | Delatorre et al. | 73/27 R |

*Primary Examiner*—Harry N. Haroian
*Attorney, Agent, or Firm*—George L. Church; Donald R. Johnson; Macka L. Murrah

[57] ABSTRACT

A detector having particular utility in a gas chromotograph uses a sensor to produce signals indicative of parameters of components of a gas. A signal whose level is related to a gas parameter is generated and sent to an amplifier. The output of the amplifier is stored and a signal related to the amplifier output signal is sent by means of a feedback loop to the input of the amplifier to compensate for losses in the amplification and storage processes.

11 Claims, 1 Drawing Figure

DETECTOR FOR A CHROMTOGRAPH

BACKGROUND OF THE INVENTION

This application is related to a co-pending application entitled ZEROING CIRCUIT Ser. No. 492,424 filed Aug. 2, 1974.

The invention relates to detecting a parameter of a component of a gas in a chromotograph, and more particularly to detecting a signal level that is indicative of the parameter.

Electrical signals are often used to carry parameters relating to many processes. Several aspects of a signal are used to represent the values of the parameters; an important one of these is the highest level which a signal attains during a particular interval of time. In gas chromotography for example, in which a gas containing molecules of different types is separated into its component parts, a signal is generated whose level is proportional to the number of molecules that pass a sensor.

The chromotograph uses a resistive medium, such as small pieces of firebrick coated with a heavy oil, to separate the gas components. A standard-sized sample of gas is carried through the medium at a constant rate by a gas such as helium. The resistive medium resists the passage of the sample gas molecules in proportion to their size. As a result the molecules of a particular size tend to bunch together and exit from the resistive medium about the same time. The smaller molecules exit first, followed by groups of molecules of progressively larger sizes. Each group of a particular size requires a known amount of time, called the elution time, to pass through the resistive medium. Each group is distributed over a small interval of time, usually in a normal or Gaussian distribution. Since the shape of the distribution is known and if the Gaussian peaks are symmetrical, the number of molecules in a group can be determined from the peak value of the distribution.

The passage of the molecules from the resistive medium is commonly sensed by a thermistor. The passage of the gas molecules over the thermistor alters the temperature of the thermistor, which in turn alters its resistance. The varying resistance is used to modulate an electrical signal. The shape of the signal will thus be related to the distribution of the molecules in a particular group separated by the resistive medium. The peak value of the signal can then be determined by means of the invention and will be a measure of the amount of the component represented by the group in the gas sample.

A peak detector commonly used in chromatography is electro-mechanical. In this device the signal from the detector is fed into the recorder and a potentiometer which varies a voltage level is connected by a shaft to the recorder mechanism. A friction switch is activated when the signal level from the detector begins to rise and remains open due to the friction as long as the signal continues to rise. However, when the signal reaches its peak and begins to fall, the frictional force subsides and the switch closes. The closing of the friction switch causes the voltage level at the output of the potentiometer to be inserted into a storage device. It is apparent that such a detector is inaccurate and difficult to maintain in proper calibration. In addition, its mechanical parts are subject to wear and tear.

It is therefore an object of the invention to provide a new and improved detector for a chromotograph that overcomes the above and other disadvantages of the prior art. Other objects become apparent as the invention is described in detail.

SUMMARY OF THE INVENTION

The invention is embodied in an apparatus that detects parameters of a component of a gas by determining the level of a signal that is indicative thereof. A detector disposed in the gas produces signals indicative of a parameter of interest. A generator produces a signal whose level bears a relationship to the signals produced by the detector and directs the signal to an amplifier. The amplifier amplifies the signal and directs it to a storage device. A signal related to that produced by the amplifier is fed back into the amplifier to correct for signal losses in the amplifier.

BRIEF DESCRIPTION OF THE DRAWINGS

The invention may be more fully understood in relation to the accompanying detailed description of the invention when read in conjunction with the following drawing.

DETAILED DESCRIPTION OF THE INVENTION

Figure 1:
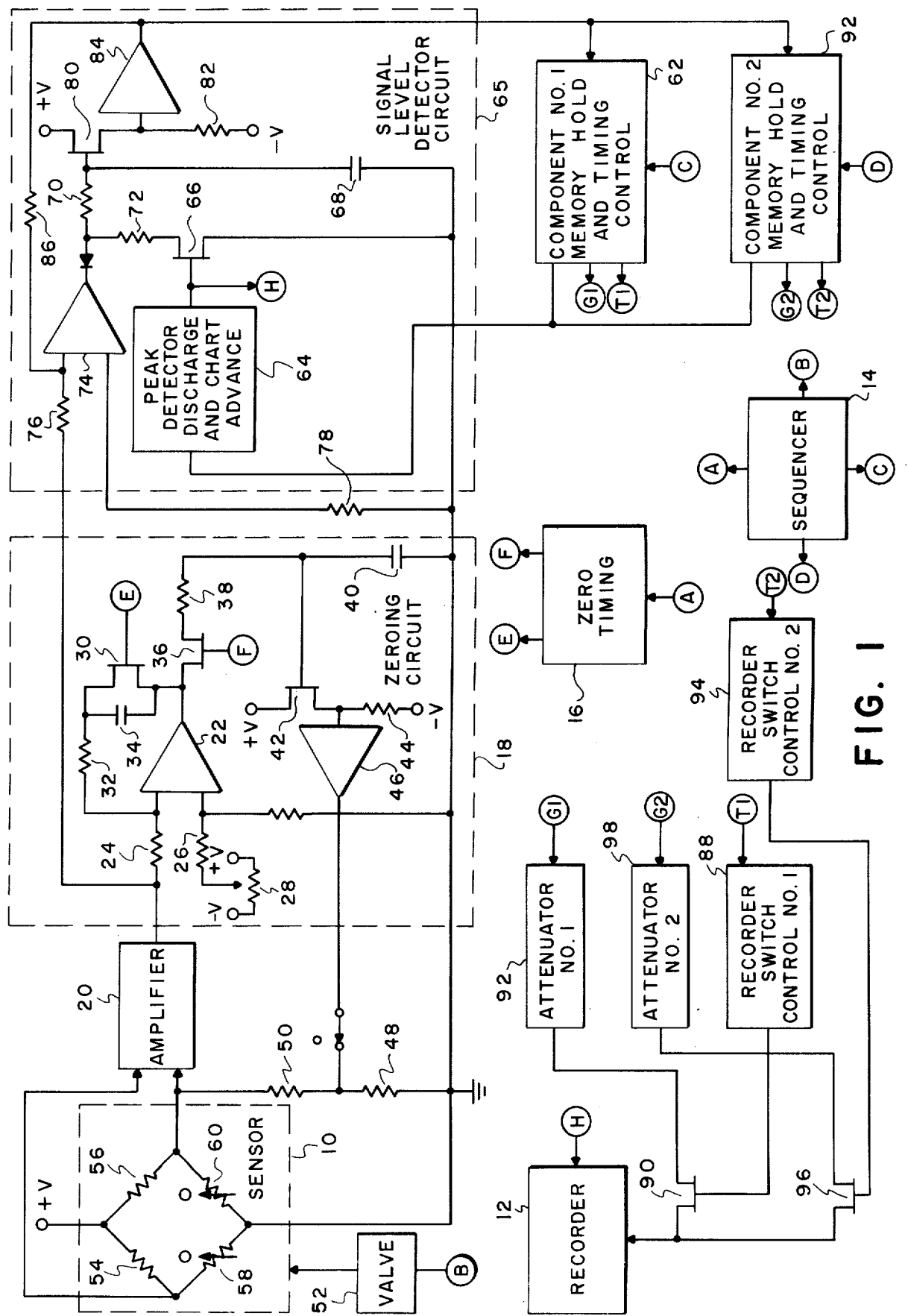
FIG. 1 is a schematic diagram of the invention.

The chromotograph control circuit shown in FIG. 1 causes the peak value of electrical signals generated by sensor 10 to be recorded on a chart by recorder 12. A sequencer 14 times the operation of various portions of the circuit to correspond to the elution time of various components of the gas sample being analyzed. For purposes of simplification of FIG. 1, a gas having only two components is assumed, although the principles of the circuit are applicable to any number of components.

Sequencer 14 begins its operation by sending signal A to zero timing circuit 16 whose output signals E and F operate zeroing circuit 18. Zeroing circuit 18 maintains the output of differential amplifier 20 at a zero level when there is no sample gas in the chromotograph. Gas currents and ambient temperatures in sensor 10 can cause signals to be sent to amplifier 20 without sample gas in the detector and for the most accurate results should be corrected for before the sample gas enters the detector. Amplifier 20 is zeroed during every cycle of the sequencer 14 in the particular control circuit shown, although it could be zeroed after every several cycles or in the midst of a cycle between the elution of individual gas components.

Zero timing circuit 16 simultaneously produces two signals of different durations, a decreasing signal E and an increasing signal F. Signals E and F can be produced by such devices as single-shot multivibrators having different time constants and opposite polarities. In the instant circuit they preferably range in level between +12 and −12 volts.

Before signals E and F reach zeroing circuit 18 and before the sample gas is injected into the chromotograph, amplifier 20 may be producing the undesired non-zero output signal. The signal enters differential amplifier 22 through a limiting resistor 24. A second signal also enters amplifier 22 through another limiting resistor 26. This signal is a constant DC signal level which compensates for offset voltage in amplifier 22. It is derived by dividing a DC signal with a potentiometer 28. The output of amplifier 22 is initially routed through a standby feedback loop which includes field-effect-transistor (FET) 30 and a resistor 32. FET 30 normally has a signal at E sufficient to maintain it in its conducting state. The feedback circuit through FET 30 serves to prevent amplifier 22 from saturating while the zeroing circuit is inactive. If saturation were allowed to occur, the time required for the amplifier to change from a saturated condition to the operating condition would delay the operation of the zeroing circuit when it is activated and thereby cause temporary undesirable oscillations. Capacitor 34 serves a similar anti-saturation function that will be discussed below.

When zero timing circuit 16 is activated by instruction A, signal E causes FET 30 to enter its non-conducting state and signal F causes another FET 36 to enter its conducting state. This opens a signal path through resistor 38 to allow capacitor 40 to be charged in relation to the level of the undesired offset signal emanating from sensor 10 through amplifier 20. The signal level stored by capacitor 40 causes FET 42 to conduct a signal through itself and a resistor 44 in proportion to the level of the signal in the capacitor 40. Due to the high input resistance of such devices, FET 42 acts as an isolator to prevent drainage of the signal from capacitor 40. An amplifier 46 amplifies the signal emanating from FET 42 and feeds the resulting signal into a resistive biasing network for amplifier 20. The biasing network includes resistors 48 and 50, and the signal from amplifier 46 enters the network between the two. Resistor 50 isolates the zeroing feedback loop from amplifier 20 to prevent its impedance characteristic from upsetting the gain of the amplifier. The feedback signal balances the input signals at the two terminals of differential amplifier 20 to produce a zero signal output with no sample gas in the chromotograph and thereby cancels the effects of an offset voltage in the detector.

Since signal E is longer in duration than signal F, FET 36 will return to its nonconducting state before FET 30 again becomes conducting and restores the standby feedback loop to operation. Thus for a period of time equal to the difference in duration of signals E and F, there will be no feedback loop connected to the output of amplifier 22. This is to prevent there being at any time a discharge path for capacitor 40 through both FET's 36 and 30 and resistor 32. To prevent the undesired saturation previously discussed, a capacitor 34 is placed across FET 30. While FET's 30 and 36 are not conducting, the signal from amplifier 22 charges capacitor 34, thereby preventing the amplifier from saturating. The capacitor with its slow charge rate satisfies the needs of the amplifier until signal E switches FET 30 to its conducting state and restores the standby feedback loop. When this occurs, the capacitor discharges through FET 30.

After amplifier 20 has been zeroed, sequencer 14 generates instruction B and sends it to valve 52, which in response, allows a gas sample of fixed quantity into sensor 10. Sensor 10 may be a resistive bridge network that includes resistors 54 and 56 and temperature variable resistors, or thermistors 58 and 60. One of the thermistors, say 60, acts as a reference. A portion of the pure carrier gas is blown across standard thermistor 60 at a constant rate. The sample gas, which is mixed with the carrier gas, moves through the resistive medium of the chromotograph, and each component thereof, after its elution time, exits from the resistive medium and moves across thermistor 58. The sample gas in mixture with the carrier gas has a different thermal conductivity from the carrier gas alone and thus removes a different amount of heat from the thermistor. The resulting difference in resistance between thermistors 58 and 60 causes a different current to flow through the resistor 54-thermistor 58 branch of the bridge than the resistor 56-thermistor 60 branch. This unbalances the bridge in an amount proportional to the quantity of sample gas passing over thermistor 60, and amplifier 20 receives a different signal from the node between resistor 54 and thermistor 58 than from the node between resistor 56 and thermistor 60. The signal differential is amplified into a proportional output signal which is sent to a signal level detector circuit 65.

During the interval between the time that the gas sample enters the chromotograph and the time that it reaches the detector, sequencer 14 generates instruction C and sends it to a memory hold and timing control circuit 62 for component No. 1 of the gas sample. Circuit 62 first sends a signal to a peak detector discharge and chart advance circuit 64 in a signal level detector circuit 65. Circuit 64 sends a signal H to recorder 12 which advances the recorder in preparation for recording the level of component No. 1. The same signal also causes FET 66 to enter its conducting state, which opens a discharge path for capacitor 68 through resistors 70 and 72 to ground potential. Capacitor 68 stores a signal whose level is porportional to the peak level of the signal generated by sensor 10 in response to the passage of a component of the gas sample and must be discharged in preparation for the next component.

After capacitor 68 has been discharged, the signal from amplifier 20 reaches one input of a differential amplifier 74 in circuit 65 through resistor 76. A second input of amplifier 74 is biased above ground potential by a resistor 78. The difference between the signal from amplifier 20 and the bias level provided by resistor 78 is amplified and sent through resistor 70 into capacitor 68. The signal level in capacitor 68 causes FET 80 to conduct a signal in proportion to that level through a resistor 82. FET 80 acts as an isolator and prevents discharge of capacitor 68. The signal appearing between FET 80 and resistor 82 is amplified by an amplifier 84. A feedback loop carries the signal back to amplifier 74 through a resistor 86. The feedback loop insures that the signal level at the input of amplifier 74 will be zero, thereby eliminating signal losses due to resistive drops in amplifier 74 and other components of circuit 65. The signal level in capacitor 68 is therefore an accurate indication of the peak level of the signal generated in detector 10.

The signal from amplifier 84 is also sent to circuit 62 where it is temporarily stored. Circuit 62 then generates a signal T1 and sends it to a recorder switch control 88 which in response causes FET 90 to conduct. At the same time the circuit 62 sends the peak level signal for component No. 1 in the form of signal G1 to an attenuator 92, which adjusts the level of the signal within the range of recorder 12. The attenuated signal is then recorded by recorder 12.

After component No. 1 has been processed, sequencer 14 generates an instruction D and sends it to memory hold and timing control circuit 92, which begins the same process for component No. 2 as for component No. 1. The recorder chart is advanced, and signal level detector circuit is cleared. The signal level is detected by circuit 65 and sent to circuit 92, which causes it to be recorded by recorder 12 using recorder switch control circuit 92, FET 96 and attenuator 98. The same process also occurs for all other components of interest.

While particular embodiments of the invention have been shown and described, it is apparent that changes and modifications could be made without departing from the true scope and spirit of the invention. It is therefore the intention in the appended claims to cover all such changes and modifications.

What is claimed is:

1. A gas chromotography circuit for detecting a parameter of a component of a gas, comprising: sensor means that produces signals indicative of parameters of the gas component; means connected to the sensor means for providing a signal whose level bears a relationship to the signals produced by the sensor means; means for amplifying the signal produced by the providing means; means for storing the amplified signal; and means for feeding back a portion of the stored signal into the amplifying means.

2. The circuit of claim 1 further including means for zeroing the signal providing means prior to the introduction of the gas to the sensor means.

3. The circuit of claim 1 wherein the signal feedback means includes means for preventing discharge of the storing means through the feedback means.

4. Circuit of claim 1 wherein the sensor means comprises a bridge network that includes temperature variable resistors.

5. Circuit of claim 4 wherein the signal providing means is a differential amplifier.

6. Circuit of claim 4 wherein the storing means is a capacitor.

7. In a gas chromotograph: gas sensor means that produces a signal in response to the presence of the gas; means for amplifying the signal; capacitor storage means communicating with the amplifying means; and electronic switch means having its gate connected to the capacitor storage means and its output connected to the input of the amplifier means.

8. A chromotograph detector circuit, comprising: bridge sensor means; means connected to the sensor means for generating a signal indicative of a parameter detected by the sensor means; an amplifier connected to the signal generating means; a capacitor connected to the output of the amplifier; a transistor connected to the output of the amplifier and the capacitor; and feedback means connected between the transistor and the input of the amplifier.

9. The circuit of claim 8 further including: a transistor connected across the capacitor and means for periodically switching the transistor to a conducting state.

10. In a gas chromotography which generates a signal that are indicative of parameters of components of a gas: an amplifier electrically communicating with the signals; a capacitor connected to the output of the amplifier; a transistor connected to the output of the amplifier and the capacitor; and a feedback loop connected between the transistor and the input of the amplifier.

11. The circuit of claim 9 further including: a transistor connected across the capacitor; and means for periodically switching the transistor to a conducting state.

* * * * *